United States Patent [19]

Singerman

[11] 4,059,699
[45] Nov. 22, 1977

[54] O,O-DIETHYL-O-CARBOXAMIDOPHOSPHATE ESTERS AND USE TO COMBAT INSECTS AND MITES

[75] Inventor: Gary M. Singerman, Allegheny County, Pa.

[73] Assignee: Gulf Oil Corporation, Pittsburgh, Pa.

[21] Appl. No.: 693,678

[22] Filed: June 7, 1976

Related U.S. Application Data

[62] Division of Ser. No. 575,866, May 9, 1975, Pat. No. 3,994,997.

[51] Int. Cl.² .............................................. A01N 9/36
[52] U.S. Cl. .................................................... 424/211
[58] Field of Search ........................ 260/944; 424/211

[56] References Cited
FOREIGN PATENT DOCUMENTS 39-26393 11/1964 Japan .................................. 260/944

*Primary Examiner*—Albert T. Meyers
*Assistant Examiner*—D. W. Robinson
*Attorney, Agent, or Firm*—Carl A. Cline

[57] ABSTRACT

Mites and insects, particularly aphids, are combated by applying as pest control agents one or more compounds of the structural formula

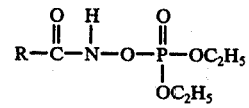

in which R is tert.butylphenyl; tert.butyl; 3,5-dimethylphenyl; 1-methyl-1-phenylthioethyl; 1-methyl-1-methylthioethyl; 1-cyclohexylthio-1-methylethyl; 1-cyclohexylthiopropyl; 1-ethylthio-1-methylethyl; 1-ethylthiopropyl or 1-ethylthioethyl.

11 Claims, No Drawings

O,O-DIETHYL-O-CARBOXAMIDOPHOSPHATE ESTERS AND USE TO COMBAT INSECTS AND MITES

This application is a division of U.S. patent application Ser. No. 575,866, filed May 9, 1975, now U.S. Pat. No. 3,994,997.

DESCRIPTION OF THE INVENTION

It is now recognized that in order to prevent the development of resistant strains of pestiferous insects and mites it is desirable to use a large number of different insecticides and change frequently from the use of one insecticide to another. It is also generally agreed that substantially complete kills increase the risk of the appearance of resistant strains and it is better to obtain only about 80 to 95 percent kills, sufficient to prevent substantial damage to crops. The injurious effect on the environment of pesticides which leave toxic inorganic residues or persist for a long period of time has also been generally recognized.

I have discovered a class of compounds which are useful for combating insects and mites, are different chemically from presently available insecticides and which decompose upon exposure to weather, leaving no toxic residues. Briefly, these novel pest control agents are compounds of the structural formula:

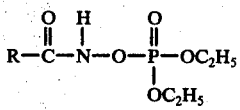

in which R is tert.butylphenyl; tert.butyl; 3,5-dimethylphenyl; 1-methyl-1-phenylthioethyl; 1-methyl-1-methylthioethyl; 1-cyclohexylthio-1-methylethyl; 1-cyclohexylthiopropyl; 1-ethylthio-1-methylethyl; 1-ethylthiopropyl or 1-ethylthioethyl.

These new insecticides provide a high degree of control of such pests as bean aphids and two-spotted mites when applied to foliage at concentrations as low as 31 ppm. It is not necessary to apply these compounds directly to the body surfaces of the insects and mites in order to obtain desirable high rates of kill and consequent substantial control. Application of an effective amount (sufficient to kill a majority of the pests) to plant foliage or other surfaces where the pests live (the locus of the pests) is sufficient. The necessary contact with the active compound occurs as a result of the normal physical activity of the pests. Two or more of the compounds may be used simultaneously. As they vary somewhat in pesticidal characteristics, the use of combinations of two or more active compounds may be preferable in some situations. The manufacture and use of the compounds is described in the discussion which follows.

PREPARATION OF THE PESTICIDES

The pesticides of this invention may be made from commercially available raw materials by means of the procedures specifically exemplified below:

Preparation of ethyl 2-methyl-2-methylthiopropionate

A solution of sodium ethoxide in ethanol was prepared from 7.2 g (0.3107 mole) sodium metal and 250 ml ethanol. This was chilled in an ice bath, and to it was added 14.9 g (0.3107 mole) methanethiol. After 5 minutes the mixture was removed from the ice bath and allowed to stand at room temperature 20 minutes. The clear, homogeneous solution was chilled in an ice bath, and to it was added 60.6 g (0.3107 mole) ethyl 2-bromoisobutyrate. Sodium bromide precipitated from the solution immediately. After 10 minutes the mixture was removed from the ice bath and was allowed to stand at room temperature 3 hours. Sodium bromide was removed from the reaction mixture by filtration. Ethanol was distilled from the filtrate at atmospheric pressure and replaced with water. The aqueous mixture was extracted with ether, and the ether extract was dried over magnesium sulfate. Magnesium sulfate was removed by filtration and the filtrate was distilled to give 43.0 g of ethyl 2-methyl-2-methylthiopropionate as a colorless oil, bp 65° at 20 mm Hg. This structure was identified by its proton magnetic resonance spectrum (pmr) which showed in CCl$_4$ solution a triplet absorption centered at 1.23 ppm ($\gamma$) and a quartet absorption centered at 4.03 $\delta$ for the protons of the ethyl group, a singlet absorption at 2.00 $\delta$ for the protons of the methylthio group, and a singlet absorption at 1.38 $\delta$ for the protons of the two remaining methyl groups.

Preparation of other ethyl 2-alkylthiopropionates, ethyl 2-arylthiopropionates, and ethyl 2-alkylthiobutyrates The following esters were prepared according to the above procedure for the preparation of ethyl 2-methyl-2-methylthiopropionate. All were identified by their pmr spectra.

1. Ethyl 2-methyl-2-phenylthiopropionate. This compound was prepared from equivalent amounts of thiophenol and ethyl 2-bromoisobutyrate. It was obtained as a light yellow oil, bp 95°–96° C at 0.35 mm Hg.

2. Ethyl 2-cyclohexylthio-2-methylpropionate. This compound was prepared from equivalent amounts of cyclohexylmercaptan and ethyl 2-bromoisobutyrate. It was obtained as a colorless liquid, bp 85° C at 0.35 mm Hg.

3. Ethyl 2-cyclohexylthiobutyrate. This compound was prepared from equivalent amounts of cyclohexylmercaptan and ethyl 2-bromobutyrate. It was obtained as colorless liquid, bp 92° C at 0.4 mm Hg.

4. Ethyl 2-methyl-2-ethylthiopropionate. This compound was prepared from equivalent amounts of ethanethiol and ethyl 2-bromoisobutyrate. It was obtained as a colorless liquid, bp 80°–85° C at 19 mm Hg.

5. Ethyl 2-ethylthiobutyrate. This compound was prepared from equivalent amounts of ethanethiol and ethyl 2-bromobutyrate. It was obtained as a colorless liquid, bp 87°–90° C at 19 mm Hg.

6. Ethyl 2-ethylthiopropionate. This compound was prepared from equivalent amounts of ethanethiol and ethyl 2-bromopropionate. It was obtained as a colorless liquid, bp 75°–82° C at 19 mm Hg.

Preparation of 2-methyl-2-methylthiopropionic acid

A mixture of 41.8 g (0.258 mole) ethyl 2-methyl-2-methylthiopropionate, 150 ml methanol, 50 ml water, and 14.6 g (0.26 mole) potassium hydroxide was stirred at room temperature overnight, then stirred and refluxed one hour. Methanol was removed from the mixture by evaporation on a rotary evaporator. The aqueous residue was acidified with 50% aqueous hydrochloric acid and extracted with ether. The ethereal extract was washed with saturated aqueous sodium chloride solution and was dried over magnesium sulfate. Magnesium sulfate was removed by filtration and ether was stripped from the filtrate on a rotatory evaporator to give colorless, crystalline 2-methyl-2-methylthiopropionic acid, mp 45°–49° C [Lit. mp 43°–47° C; J. A. Durden, Jr. et al., J. Agr. Food Chem., 18 (3), 454 (1970)].

Preparation of other 2-alkylthio- and 2-arylthiopropionic acids and 2-alkylthiobutyric acids The following acids were prepared as just described for the preparation of 2-methyl-2-methylthiopropionic acid.

1. 2-Methyl-2-phenylthiopropionic acid, colorless crystals, mp 63°–65.5° C, by hydrolysis of ethyl 2-methyl-2-phenylthiopropionate.

2. Cyclohexylthio-2-methylpropionic acid, colorless crystals, mp 58°–65° C, by hydrolysis of ethyl 2-cyclohexylthio-2-methylpropionate.

3. 2-Cyclohexylthiobutyric acid, colorless crystals, by hydrolysis of ethyl 2-cyclohexylthiobutyrate.

4. 2-Methyl-2-ethylthiopropionic acid, by hydrolysis of the corresponding ethyl ester. This structure was identified by its pmr spectrum.

5. 2-Ethylthiobutyric acid, by hydrolysis of the corresponding ethyl ester. This structure was identified by its pmr spectrum.

Preparation of 2-methyl-2-methylthiopropionyl chloride

A solution of 29.0 g 2-methyl-2-methylthiopropionic acid and 100 ml thionyl chloride was allowed to stand at room temperature one hour. Thionyl chloride (45 ml) was removed by distillation on a steam bath, bp 76°–77° C at atmospheric pressure over 1.5 hours. The remainder of the thionyl chloride was removed by distillation at 120 mm Hg (bp 36° C) and the title compound was then obtained as a colorless liquid, bp 65°–68° C at 25 mm Hg. [Lit. bp 54.5°–58° C at 13 mm Hg; J.A. Durden, Jr. et al., J. Agr. Food Chem., 18 (3), 454 (1970)]. This structure was identified by its pmr spectrum which showed in CCl$_4$ solution a singlet absorption at 2.00 $\delta$ for the protons of the methylthio group, and a singlet absorption at 1.53 $\delta$ for the protons of the two remaining methyl groups.

Preparation of other acid chlorides

The following acid chlorides were prepared from the corresponding acids in a manner similar to that described for the preparation of 2-methyl-2-methylthiopropionyl chloride, and were identified by their pmr spectra.

1. 2-Methyl-2-phenylthiopropionyl chloride, colorless liquid, bp 92° C at 0.35 mm Hg.

2. 2-Cyclohexylthio-2-methylpropionyl chloride, colorless liquid , bp 92° C at 0.7 mm Hg.

3. 2-Cyclohexylthiobutyryl chloride, colorless liquid, bp 78° C at 0.4 mm Hg.

4. 2-Methyl-2-ethylthiopropionyl chloride, colorless liquid, bp 75° C at 25 mm Hg.

5. 2-Ethylthiobutyryl chloride, colorless liquid, bp 82° C at 25 mm Hg.

6. 2-Ethylthiopropionyl chloride, colorless liquid, bp 72° C at 25 mm Hg.

7. 3,5-Dimethylbenzoyl chloride, colorless oil, bp 100° C at 3.5 mm Hg.

Preparation of 2-Methyl-2-methylthiopropionohydroxamic acid

Hydroxylamine hydrochloride (13.9 g, 0.2 mole) was dissolved in a minimum of methanol. In a second container potassium hydroxide (11.2 g, 0.2 mole) was likewise dissolved in a minimum of methanol. Both solutions were chilled to 0° C in a dry ice-acetone bath and the methanolic potassium hydroxide solution was added to the methanolic hydroxylamine hydrochloride. Potassium chloride precipitated from the solution immediately and was removed by suction filtration. The filtrate, containing methanol and hydroxylamine, was cooled to 0° C and to it was added 15.3 g (0.1 mole) 2-methyl-2-methylthiopropionyl chloride. The mixture was removed from the ice bath and stirred magnetically for 4 hours at room temperature. Solids were removed from the reaction mixture by suction filtration and methanol was stripped from the filtrate on a rotatory evaporator. Water (100 Ml) was added to the residue and white, solid 2-methyl-2-methylthiopropionohydroxamic acid (3.5 g) was isolated by suction filtration, mp 119°–122° C after air-drying overnight. [Lit. mp 128°–132° C (benzene-cyclohexane); J.A. Durden, Jr. et al, J. Agr. Food Chem., 18 (3), 454 (1970)]. The aqueous filtrate was evaporated to ca. 25 ml and allowed to stand overnight to precipitate an additional 2.3 g of product. The product gave a strong positive ferric chloride test, characteristic of hydroxamic acids [R. L. Shriner, et al., Systematic Identification of Organic Compounds, Ed. 4, John Wiley and Sons, Inc., 1956, p. 122].

Preparation of other hydroxamic acids

The following hydroxamic acids were prepared from the corresponding acid chlorides in a manner similar to that described for the preparation of 2-methyl-2-methylthiopropionohydroxamic acid. Each hydroxamic acid gave a characteristic positive ferric chloride test.

1. 2-Methyl-2-phenylthiopropionohydroxamic acid, colorless solid, mp 122°–125° C. In addition to giving a strong positive ferric chloride test, this structure was identified by its pmr spectrum.

2. 2-Cyclohexylthio-2-methylpropionohydroxamic acid, white solid, mp not recorded.

3. 2-Cyclohexylthiobutyrohydroxamic acid, white solid, mp not recorded.

4. 2-Methyl-2-ethylthiopropionohydroxamic acid, white solid, mp not recorded.

5. 2-Ethylthiobutyrohydroxamic acid, white solid, mp not recorded.

6. 2- Ethylthiopropionohydroxamic acid, white solid, mp not recorded.

7. 3,5-Dimethylbenzoyhydroxamic acid, white solid, mp not reocrded.

8. 4-t-Butylbenzohydroxamic acid, white solid, mp 141°–144° C.

9. Trimethylacetohydroxamic acid, white solid, mp 165°–167° C, identified by pmr.

EXAMPLE 1

Preparation of O,O-diethyl-O-(2-methyl-2-methylthiopropionamido)-phosphate

To a solution of 3.5 g (0.0235 mole) 2-methyl-2-methylthiopropionohydroxamic acid and 50 ml dry tetrahydrofuran was added 0.024 mole sodium hydride (1.0 g of 57% oil dispersion, washed with hexane before use). The mixture was stirred one hour at room temperature, and to it was added 4.2 g (0.024 mole) diethyl chlorophosphate. The mixture was stirred at room temperature overnight and tetrahydrofuran was then stripped from it on a rotatory evaporator and replaced with water. The aqueous mixture was made basic with sodium bicarbonate and extracted with ether. The ethereal extract was dried over magnesium sulfate. Magnesium sulfate was removed by filtration and ether was stripped from the filtrate on a rotatory evporator to give the title compound as a yellow oil. This structure was identified by its pmr spectrum which showed in CDCl$_3$ solution a triplet absorption centered at 1.35 δ and a complex multiplet centered at 4.18 δ for the protons of the ethyl groups, a singlet absorption at 1.67 δ for the protons of the two methyl groups, and a singlet absorption at 2.12 δ for the protons of the methylthio group.

Preparation of other O,O-diethyl-O-amidophosphates

The following phosphate esters were prepared from diethyl chlorophosphate and the appropriate hydroxamic acid as described for the preparation of O,O-diethyl-O-(2-methyl-2-methylthiopropionamido)phosphate.

EXAMPLE 2

O,O-diethyl-O-(2-methyl-2-phenylthiopropionamido)phosphate, a light yellow oil. Its pmr spectrum in CDCl$_3$ shows multiplet absorptions centered at 1.50 δ, 4,17 δ, and 7.25 δ.

EXAMPLE 3

O,O-diethyl-O-(2-cyclohexylthio-2-methylpropionamido)phosphate, oil; pmr spectrum (CCl$_4$) δ 1.20–1.50 (triplet), 1.67 (singlet), 1.20–217 (broad envelope), and 3,87–4.42 (multiplet).

EXAMPLE 4

O,O-diethyl-O-(2-cyclohexylthiobutyramido) phosphate, oil; pmr spectrum (CCL$_4$) δ 1.20–1.50 (triplet), 0.73–2.18 (complex), 2.18–3.70 (complex), and 3.83–4.37 (complex).

EXAMPLE 5

O,O-diethyl-O-(2-methyl-2-ethylthiopropionamido)-phosphate, oil; pmr spectrum (CCl$_4$) δ 1.07–1.80 (complex), 2.37–2.90 (quartet), and 3.87–4.43 (complex).

EXAMPLE 6

O,O-diethyl-O-(2-ethylthiobutyramido)phosphate, oil; pmr spectrum (CCl$_4$) δ 0.83–2.13 (complex), 2.33–2.73 (quartet), 2.80–3.17 (complex),and 3.87–4.43 (complex).

EXAMPLE 7

O,O-diethyl-O-(2-ethylthiopropionamido)phospate, oil; pmr spectrum (CCl$_4$) δ 1.07–1.70 (complex), 2.33–2.87 (quartet), 3.17–3.63 (quartet), and 3,83–4.47 (complex).

EXAMPLE 8

O,O-diethyl-O-(3,5-dimethylbenzamido)phosphate, oil; pmr spectrum (CDCl$_3$) δ 1.13–1.57 (triplet), 2.22 (singlet), 2.32 (singlet), 3.90–4.47 (complex), and 6.33–7.67 (complex).

EXAMPLE 9

O,O-diethyl-O-(4-t-butylbenzamido)phosphate, solid; pmr spectrum (CDCl$_3$) δ 1.22–1.57 (complex), 4.00–4.53 (complex), and 7.25–8.17 (complex).

EXAMPLE 10

O,O-diethyl-O-(trimethylacetamido)phosphate, oil; pmr spectrum (CDCl$_3$) δ 1.25 (singlet), 1.27–1.48 (triplet), and 4.00–4.50 (complex).

COMBATING INSECTS AND MITES

Illustrative use of the pesticides of this invention was made according to the procedure set forth below.

PROCEDURE

1. Place three 5 oz Dixie cups containing one Henderson bush lima bean plant per cup on the turntable. Place each cup by itself on one of the turntable holders, of which there are four. One of the bean plants has already been infested the day before with 50–100 two-spotted mites. Place one 5 oz Dixie cup containing Orange Gem nasturtiums already infested the week before with 50–100 bean aphids on the turntable.

2. Formulate candidate sample of insecticide to 500 ppm by dissolving 25 mg of sample in 5 ml of acetone, adding to 50 ml mark warm aqueous Triton X-100 solution containing 1.2 ml (60 drops) Triton X-100 (octylphenoxy polyethoxyethanol) per liter and shaking. Pour the formulated solution into a 1¾ oz Dixie cream cup and place on the holder in the spray hood. The siphon tube is adjusted so that approximately 25 ml of spray solution is sprayed on the plants on the turntable.

3. Close hood sash, and turn on sprayer, stirrer, turntable and hood fan switches. Spray plants to thorough wetness.

4. Remove sprayed plants from turntable and place on lab trays for transfer to holding rooms. Place aphid-infested nasturtiums on cards on the shelves. The cards are stamped with the candidate S-number. Place mite infested bean plants on cards also. Clip both primary leaves from one of the sprayed uninfested bean plants and place wad of absorbent cotton around cut petioles. Saturate cotton with water. Place leaves in numbered disposable plastic petri dish. Count 5 southern armyworm larvae onto leaves in dish and cover with lid. Clip one primary leaf from the remaining uninfested bean plant and provide cut petiole with wet cotton. Place leaf in a numbered petri dish. Count 5 Mexican bean beetle larvae onto the leaf in the dish and cover with lid.

5. Determine mortality of bean aphids by the following morning, and the mortality of the southern armyworms, bean beetle larvae and mites two days later. Use the following rating system:

| MBB | BA |
|---|---|
| 0 = none dead | 0 = none dead |
| 1–5 = 1–5 larvae dead | 1 = 1–25% dead |
|  | 2 = 26–50% dead |
|  | 3 = 51–75% dead |
|  | 4 = 76–99+% dead |
|  | 5 = 100% dead |
| SA | TSM |
| 0 = none dead | 0 = no dead adults |
| 1–5 = 1–5 larvae dead | 1 = 1–25% dead adults |
|  | 2 = 26–50% dead adults |
|  | 3 = 51–75% dead adults |
|  | 4 = 76–99%+ dead adults |
|  | 5 = 100% dead adults |

Data obtained by means of the procedure outlined above are summarized in the following table.

TABLE 1
INSECTICIDAL ACTIVITY

| Structure | | Concentration (ppm) | | | | | |
|---|---|---|---|---|---|---|---|
| | | | 500 | 250 | 125 | 62 | 31 | 15 |
| $(CH_3)_3CC_6H_4CNHOP(OC_2H_5)_2$ with two C=O | MBB | 0 | | | | | |
| | SA | 0 | | | | | |
| | BA | 5 | 5 | 5 | 5 | 3 | 1 |
| | TSM | 3 | 5 | 5 | 5 | 4 | 4 |
| $(CH_3)_3CCNHOP(OC_2H_5)_2$ | MBB | 0 | | | | | |
| | SA | 3 | | | | | |
| | BA | 5 | 5 | 5 | 5 | 5 | 5 |
| | TSM | 5 | 4 | 2 | 2 | 1 | 0 |
| 3,5-dimethylphenyl-CNHOP(OC_2H_5)_2 | MBB | 0 | | | | | |
| | SA | 0 | | | | | |
| | BA | 5 | 5 | 5 | 5 | 4 | 1 |
| | TSM | 5 | 5 | 5 | 4 | 3 | 3 |
| $C_6H_5SC(CH_3)_2CNHOP(OC_2H_5)_2$ | MBB | 0 | | | | | |
| | SA | 0 | | | | | |
| | BA | 5 | 5 | 5 | 4 | 4 | 1 |
| | TSM | 2 | | | | | |
| $CH_3-C(CH_3)(SCH_3)-CNHOP(OC_2H_5)_2$ | MBB | 5 | 5 | 5 | 4 | 0 | 0 |
| | SA | 0 | | | | | |
| | BA | 4 | 5 | 5 | 5 | 5 | 2 |
| | TSM | 5 | 5 | 5 | 5 | 5 | 5 |
| cyclohexyl-S-C(CH_3)_2-CNHOP(OC_2H_5)_2 | MBB | 4 | 5 | 0 | 0 | 0 | 0 |
| | SA | 3 | 2 | 0 | 0 | 0 | 0 |
| | BA | 4 | 2 | 0 | 0 | 0 | 0 |
| | TSM | 5 | 5 | 5 | 5 | 5 | 5 |
| cyclohexyl-S-CH(CH_2CH_3)CNHOP(OC_2H_5)_2 | MBB | 0 | | | | | |
| | SA | 0 | | | | | |
| | BA | 5 | 2 | 2 | 1 | 0 | 0 |
| | TSM | 5 | 5 | 5 | 5 | 4 | 3 |
| $CH_3-C(CH_3)(SCH_2CH_3)-CNHOP(OC_2H_5)_2$ | MBB | 0 | | | | | |
| | SA | 0 | | | | | |
| | BA | 5 | 5 | 5 | 5 | 4 | 0 |
| | TSM | 5 | 5 | 4 | 4 | 4 | 4 |
| $CH_3CH_2CH(SCH_2CH_3)CNHOP(OC_2H_5)_2$ | MBB | 3 | 3 | 4 | 0 | 0 | 0 |
| | SA | 0 | | | | | |
| | BA | 5 | 5 | 5 | 5 | 4 | 2 |
| | TSM | 5 | 5 | 5 | 4 | 3 | 3 |
| $CH_3CH(SCH_2CH_3)CNHOP(OC_2H_5)_2$ | MBB | 0 | | | | | |
| | SA | 0 | | | | | |
| | BA | 4 | 5 | 5 | 4 | 2 | 0 |
| | TSM | 5 | 5 | 5 | 4 | 4 | 4 |

I claim:

1. A method of combating insects and mites comprising applying to the locus of the insects and mites an effective amount, sufficient to kill a majority of said insects and mites of a compound of the structural formula: ,03/0010

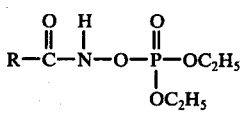

in which R is selected from the group consisting of tert.butyl; 3,5-dimethylphenyl; 1-methyl-1-phenylthioethyl; 1-methyl-1-methylthioethyl; 1-cyclohexylthio-1-methylethyl; 1-cyclohexylthiopropyl; 1-ethylthio-1-methylethyl; 1-ethylthiopropyl and 1-ethylthioethyl.

2. A method of combating insects and mites comprising applying to the locus of the insects and mites an effective amount, sufficient to kill a majority of said insects and mites of O,O-diethyl-O-(2-methyl--2-methylthiopropionamido)phosphate.

3. A method of combating insects and mites comprising applying to the locus of the insects and mites an effective amount, sufficient to kill a majority of said insects and mites of O,O -diethyl-O-(2-methyl-2-phenyl-thiopropionamido)phosphate.

4. A method of combating insects and mites comprising applying to the locus of the insects and mites an effective amount, sufficient to kill a majority of said insects and mites of O,O-diethyl-O-(2-cyclohexylthio-2-methylpropionamido)-phosphate.

5. A method of combating insects and mites comprising applying to the locus of the insects and mites an effective amount, sufficient to kill a majority of said insects and mites of O,O-diethyl-O-(2-cyclohexylthiobutyramido)phosphate.

6. A method of combating insects and mites comprising applying to the locus of the insects and mites an effective amount, sufficient to kill a majority of said insects and mites of O,O-diethyl-O-(2-methyl-2-ethylthiopropionamido)phosphate.

7. A method of combating insects and mites comprising applying to the locus of the insects and mites an effective amount, sufficient to kill a majority of said insects and mites of O,O-diethyl-O-(2-dethylthiobutyramido)phosphate.

8. A method of combating insects and mites comprising applying to the locus of the insects and mites an effective amount, sufficient to kill a majority of said insects and mites of O,O-diethyl-O-(2-ethylthiopropionamido)phosphate.

9. A method of combating insects and mites comprising applying to the locus of the insects and mites an effective amount, sufficient to kill a majority of said insects and mites of O,O-diethyl-O-(3,5-dimethylbenzamido)phosphate.

10. A method of combating insects and mites comprising applying to the locus of the insects and mites an effective amount, sufficient to kill a majority of said insects and mites of O,O-diethyl-O-(4-t-butylbenzamido)phosphate.

11. A method of combating insects and mites comprising applying to the locus of the insects and mites an effective amount, sufficient to kill a majority of said insects and mites of O,O-diethyl-O-(trimethylacetamido)phosphate.

* * * * *

UNITED STATES PATENT AND TRADEMARK OFFICE
CERTIFICATE OF CORRECTION

PATENT NO. : 4,059,699

DATED : November 22, 1977

INVENTOR(S) : Gary M. Singerman

It is certified that error appears in the above-identified patent and that said Letters Patent are hereby corrected as shown below:

Column 2, line 19, should read "tion centered at 1.23 ppm ($\delta$) and a quartet absorption".

Column 5, line 30, should read "1.50 $\delta$, 4.17 $\delta$, and 7.25 $\delta$."

Column 5, line 36, should read "lope), and 3.87-4.42(multiplet)."

Column 5, line 40, should read "phate, oil; pmr spectrum ($CCl_4$) $\delta$ 1.20-1.50 (triplet),".

Column 5, line 57, should read "2.33-2.87(quartet), 3.17-3.63 (quartet), and 3.83-4.47".

Column 6, line 38, should read "leaves from one of the sprayed uninfested bean plants".

Column 6, line 39, should read "and place wad of absorbent cotton around cut petioles."

Column 6, line 63, should read " 1-5 = 1-5 larvae dead 1 = 1-25% dead adults".

Column 7, line 54, "03/0010" should be deleted.

Column 9, line 6, should read "insects and mites of O,O-diethyl-O-(2-ethylthi-"

Signed and Sealed this

Eighteenth Day of April 1978

[SEAL]

Attest:

RUTH C. MASON
Attesting Officer

LUTRELLE F. PARKER
Acting Commissioner of Patents and Trademarks